United States Patent [19]

Nakatsuka et al.

[11] Patent Number: 5,324,704

[45] Date of Patent: * Jun. 28, 1994

[54] FLUORAN COMPOUNDS, CRYSTALLINE TOLUENE ADDUCTS THEREOF, RECORDING MATERIAL COMPRISING SAME AND PROCESS FOR THEIR PREPARATION

[75] Inventors: Masakatsu Nakatsuka, Yokohoma; Atsuo Otsuji, Kamakura; Kiyoharu Hasegawa, Yokohama; Masatoshi Takagi; Akihiro Yamaguchi, both of Kamakura, all of Japan

[73] Assignee: Mitsui Toatsu Chemicals, Inc., Tokyo, Japan

[*] Notice: The portion of the term of this patent subsequent to Mar. 16, 2010 has been disclaimed.

[21] Appl. No.: 37,847

[22] Filed: Mar. 29, 1993

Related U.S. Application Data

[62] Division of Ser. No. 553,834, Jul. 18, 1990, Pat. No. 5,220,038.

[30] Foreign Application Priority Data

| | | | |
|---|---|---|---|
| Jul. 19, 1989 | [JP] | Japan | 1-184718 |
| Aug. 1, 1989 | [JP] | Japan | 1-197949 |
| Feb. 16, 1990 | [JP] | Japan | 2-33816 |

[51] Int. Cl.$^5$ .................. B41M 5/20; C07D 311/78
[52] U.S. Cl. .................. 503/220; 503/221; 549/223; 549/224; 549/226
[58] Field of Search ........... 549/223, 224, 225, 226; 503/220, 221

[56] References Cited

U.S. PATENT DOCUMENTS

| | | | |
|---|---|---|---|
| 4,694,088 | 9/1987 | Kaneko et al. | 549/226 |
| 5,194,632 | 3/1993 | Nakatsuka et al. | 549/224 |

FOREIGN PATENT DOCUMENTS

| | | |
|---|---|---|
| 0176161 | 4/1986 | European Pat. Off. . |
| 0207635 | 1/1987 | European Pat. Off. . |
| 0220515 | 5/1987 | European Pat. Off. . |
| 48-43296 | 12/1973 | Japan . |
| 51-23204 | 7/1976 | Japan . |
| 54-34909 | 3/1979 | Japan . |
| 58-096588A | 6/1983 | Japan . |
| 59-197463 | 9/1984 | Japan . |
| 60-141762A | 7/1985 | Japan . |
| 60-202155A | 10/1985 | Japan . |
| 2141727A | 1/1985 | United Kingdom . |

*Primary Examiner*—Mukund J. Shah
*Assistant Examiner*—Y. N. Gupta
*Attorney, Agent, or Firm*—Millen, White, Zelano & Branigan

[57] ABSTRACT

Disclosed are novel fluoran compounds represented by the formula (I):

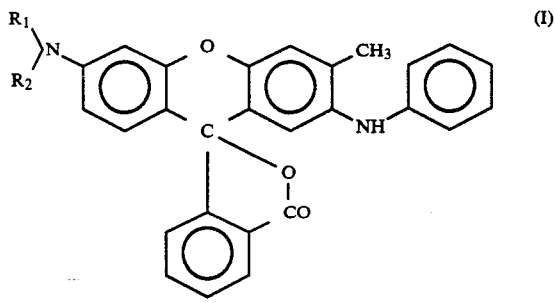

wherein $R_1$ and $R_2$ are different groups selected from cyclohexyl, n-butyl and isobutyl, e.g., in the form of crystals characterized by a specific X-ray diffraction diagram; crystalline toluene adducts thereof; and recording materials containing these fluoran compounds.

13 Claims, 5 Drawing Sheets

FLUORAN COMPOUNDS, CRYSTALLINE TOLUENE ADDUCTS THEREOF, RECORDING MATERIAL COMPRISING SAME AND PROCESS FOR THEIR PREPARATION

This is a division of application Ser. No. 07/553,834, filed Jul. 18, 1990, now U.S. Pat. No. 5,220,038.

BACKGROUND OF THE INVENTION

1) Field of the Invention

The present invention relates to novel fluoran compounds which are useful as chromogenic compounds in recording materials such as pressure sensitive and heat-sensitive recording materials. More particularly, the invention relates to crystal of a fluoran compounds in crystalline form, to crystalline toluene adducts thereof, to a process for the preparation of these compounds and to recording materials comprising these compounds.

2) Description of the Prior Art

Pressure-sensitive recording, heat-sensitive recording and electroheat-sensitive recording have conventionally been used as systems for recording transfered information through the mediation of external energy, such as pressure, heat or electricity, by utilizing a color reaction between a colorless or pale colored electron donative compound (chromogenic compound) and an organic or inorganic electron acceptor (developer).

In these systems, fluoran compounds have widely been used as the chromogenic compound.

Many fluoran compounds are known in the prior art, including those having structures similar to the fluoran compounds of the invention, for example, those having the formulas (A), (B), (C), (D) and (E).

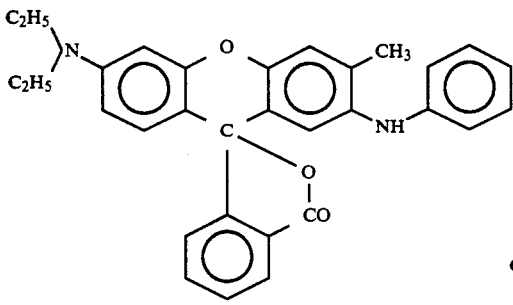

(A)

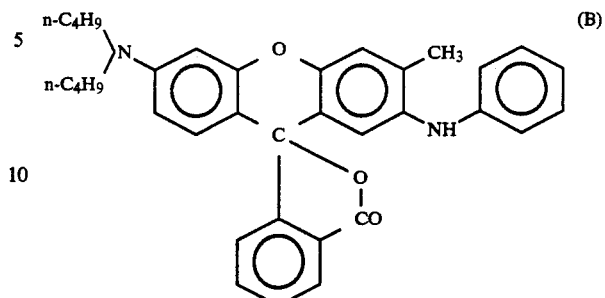

(B)

Japanese Patent Laid-Open Publication SHO 48-43296(1973)

Japanese Patent Laid-Open Publication SHO 48-43296(1973)
Japanese Patent Laid-Open Publication SHO 60-202155(1985)

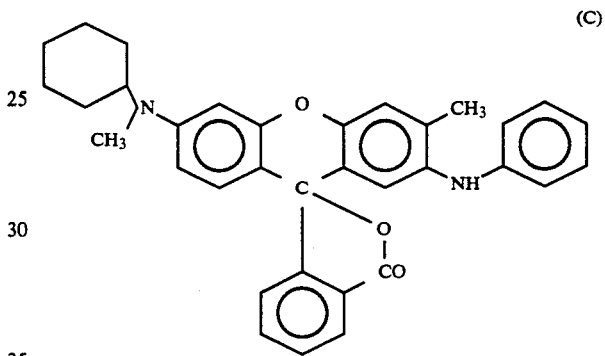

(C)

Japanese Patent Laid-Open Publication SHO 48-23204(1973)

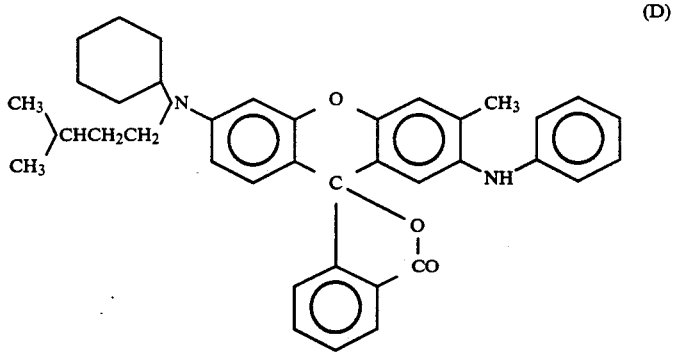

(D)

Japanese Patent Laid-Open Publication SHO 54-34909(1979)

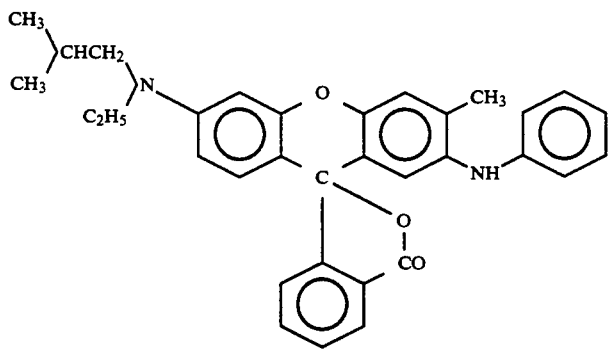

Japanese Patent Laid-Open Publication SHO 59-197463(1984)

However, the compound of the formula (A) has the disadvantage of very low solubility in capsule oil when the compound is used in a pressure-sensitive recording material. Additionally, in the case of applying to the heat-sensitive recording material, the compound has the defect that the compound itself colors gray to dark gray when mixed with a developer such as bisphenol A and provide only a gray to dark gray colored (soiled) paper by applying the mixture to a paper.

The chromogenic temperatures of the compounds of formulas (B), (C), (D) and (E) are too high to permit their use in a heat-sensitive recording material. Consequently, the performance of these prior art compounds cannot fully meet the present market demand for more rapid and higher density recording. Therefore, a chromogenic compound capable of quickly developing color at a lower temperature has been strongly desired.

Further, the compounds of formulas (A)–(E) are poorly soluble in capsule oil and their performance is still unsatisfactory for the pressure-sensitive recording material.

OBJECTS OF THE INVENTION

One object of the present invention is to provide novel fluoran compounds capable of meeting the current performance demands as a chromogenic compound for use in the recording materials.

Another object of the present invention is to provide crystalline forms of novel fluoran compounds having further improved functional properties when used in recording materials.

A further object of the present invention is to provide a process for the preparation of the novel fluoran compounds and specific crystalline forms of these compounds.

Still another object of the present invention is to provide recording materials comprising a novel fluoran compound of this invention, especially those comprising a specific crystal form of the compound.

SUMMARY OF THE INVENTION

In a composition aspect, the present invention relates to novel fluoran compounds represented by Formula (I):

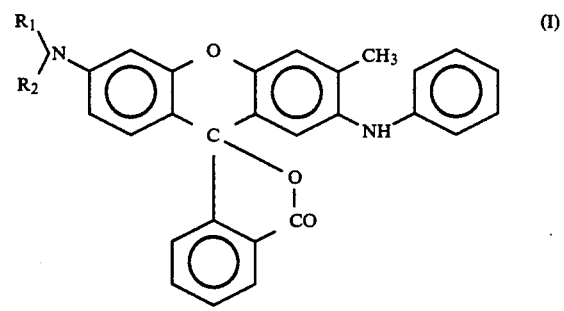

wherein $R_1$ and $R_2$ are different groups selected from cyclohexyl, n-butyl and isobutyl.

In a process aspect, this invention relates to a process for the preparation of the fluoran compounds of this invention by reacting a benzoic acid derivative represented by Formula (II):

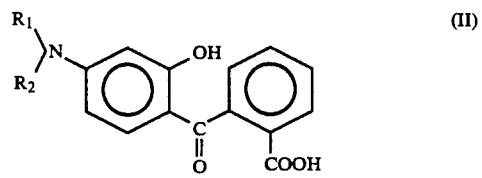

wherein $R_1$ and $R_2$ are the same as in Formula (I), with a diphenylamine derivative represented by Formula (III):

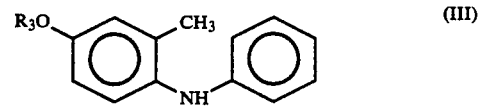

wherein $R_3$ is a lower alkyl group.

In other composition aspects, this invention relates to the fluoran compounds of this invention in crystalline form, which crystals are characterized by a specific X-ray diffraction diagram and is represented by Formula (I); to crystalline solvated adducts, e.g., toluene adducts, of the fluoran compounds of this invention, which crystals are characterized by a specific X-ray diffraction diagram; and to recording materials comprising a fluoran compound or specific crystal or crystalline toluene adducts of a fluoran compound of this invention.

In each of the above drawings, axis of abscissa indicates angle of diffraction ($2\theta$) and axis of ordinate indicates strength of diffraction.

Figure 8:
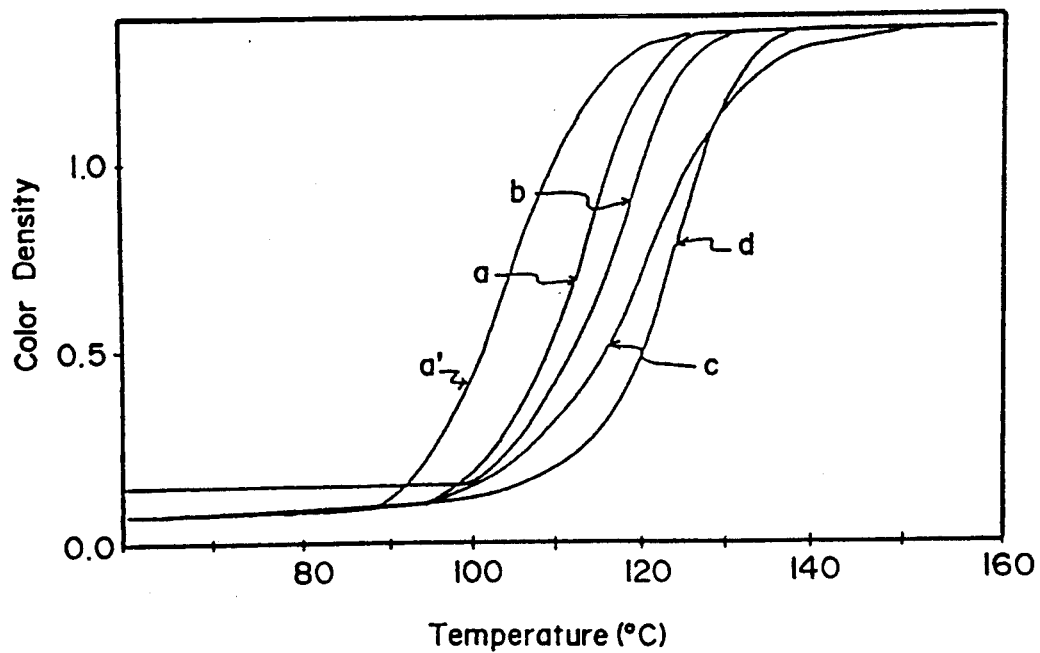

FIG. 8 illustrates color density characteristics to temperature change on the surface of heat-sensitive recording paper prepared using the Type I crystalline form of the compound represented by Formula (I-1), the Type II crystalline form of the crystalline toluene adduct of the compound represented by Formula (I-1); and a known fluoran compound.

In FIG. 8, curve (a) illustrates color density characteristic of Type 1 crystal; curve (a'), that of Type II crystal; curve (b), that of the compound of Formula (A); curve (c), that of the compound of Formula (B); and curve (d), that of the compound of Formula (C), respectively.

Figure 9:
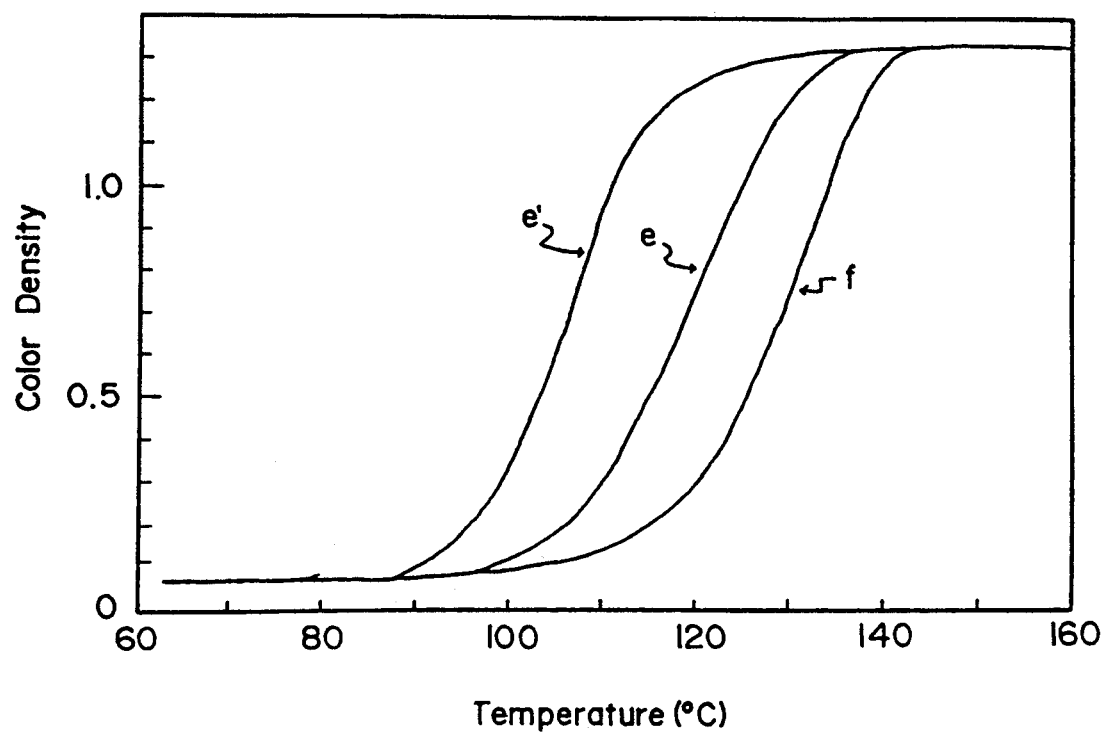

FIG. 9 illustrates color density characteristics in relation ship to temperature change on the surface of heat-sensitive recording paper prepared using Type III crystal of the compound represented by Formula (I-2), using Type IV crystal of the crystalline toluene adduct of the compound represented by formula (I-2), and using a known fluoran compound, respectively.

In FIG. 9, curve (e) illustrates the color density characteristic of the Type III crystalline form, curve (e') illustrates that of the Type IV crystalline form, and curve (f) illustrates that of the compound of Formula (D).

Figure 10:
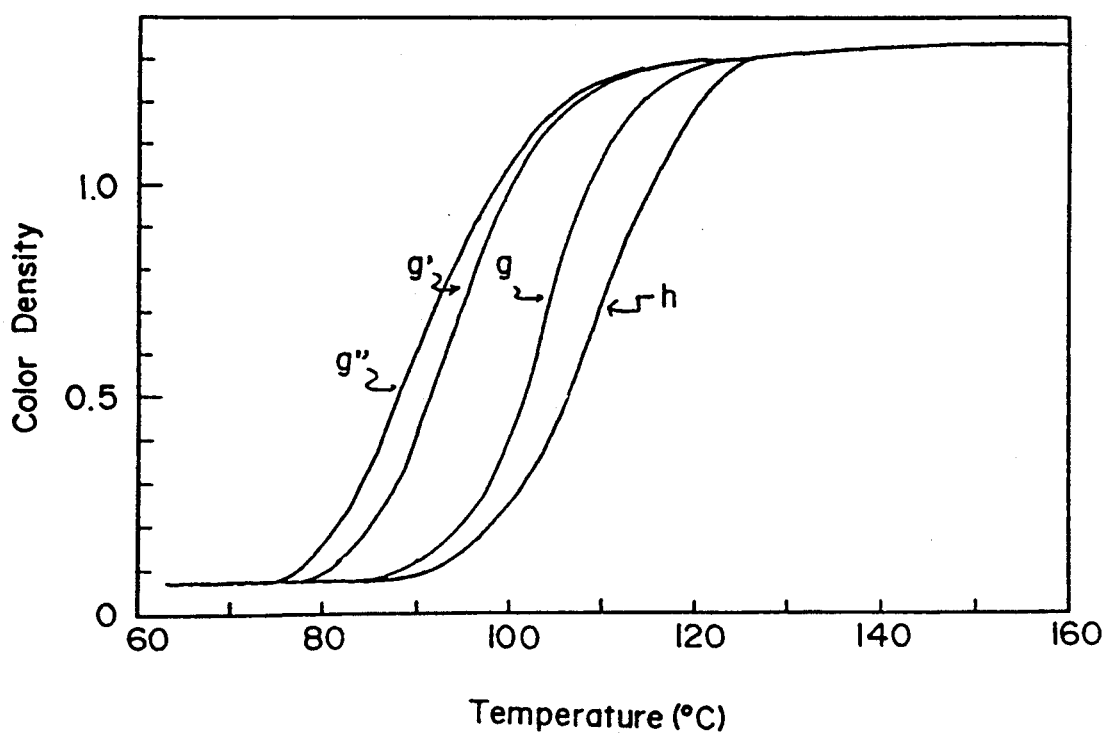

FIG. 10 illustrates color density characteristics relative to temperature change on the surface of heat-sensitive recording paper prepared using the Type V crystalline form of the compound represented by formula (I-3), using the Type VI crystalline form of the crystalline toluene adduct of the compound represented by the formula (I-3), using the Type VII crystalline form of another crystalline toluene adduct of the compound represented by Formula (I-3), and using a known fluoran compound.

In FIG. 10, curve (g) illustrates the color density characteristic of the Type V crystalline form, curve (g') illustrates that of the Type VI crystalline form, curve (g") illustrates that of the Type VII crystalline form, and the curve (h) illustrates that of the compound of formula (E), respectively.

DETAILED DESCRIPTION OF THE INVENTION

The fluoran compounds of the present invention include compounds having the structural Formulas (I-1), (I-2) and (I-3):

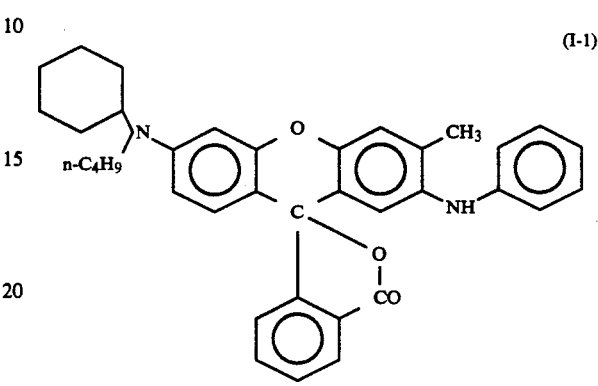
(I-1)

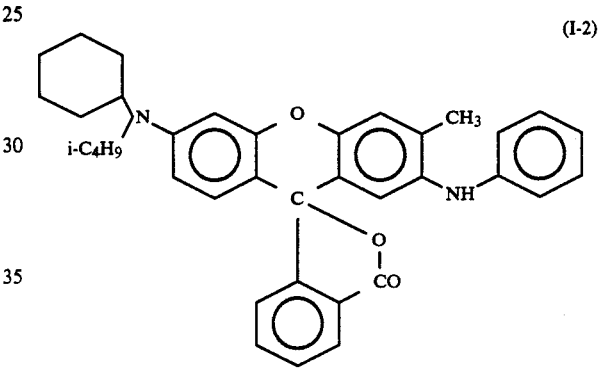
(I-2)

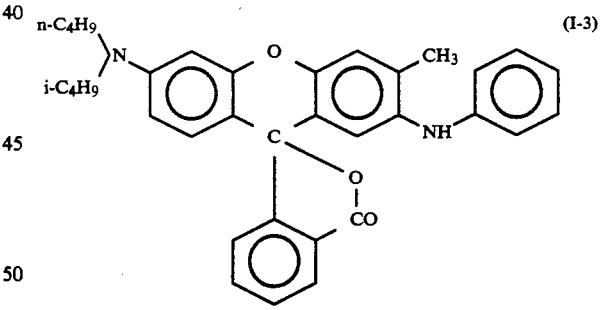
(I-3)

The fluoran compounds of this invention can be prepared by reacting an benzoic acid derivative represented by Formula (II):

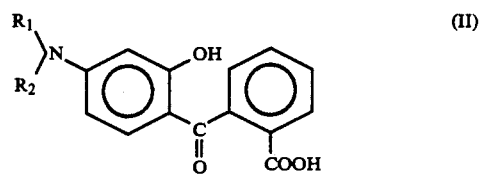
(II)

wherein $R_1$ and $R_2$ are the same as in Formula (I), e.g., compounds of formula (II-1), (II-2) or (II-3):

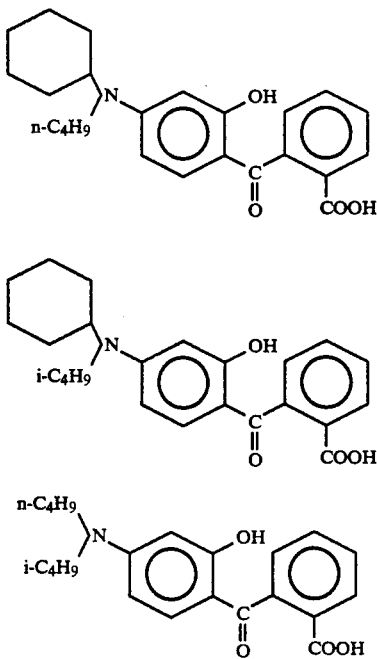

(II-1)

(II-2)

(II-3)

with a diphenylamine derivative represented by Formula (III):

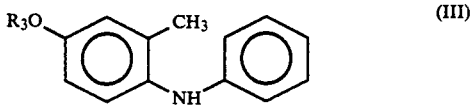

(III)

wherein $R_3$ is a lower alkyl group, in the presence of a dehydrating condensation agent, for example, concentrated sulfuric acid, mixture of oleum and concentrated sulfuric acid, polyphosphoric acid, phosphorus pentaoxide and anhydrous aluminum chloride, preferably concentrated sulfuric acid, and thereafter bringing the reaction mixture to an alkaline pH.

The time and temperature of the dehydrating condensation reaction is not critical and is usually carried out at 0° to 100° C. for from several hours to 100 hours. When the reaction is carried out in concentrated sulfuric acid, the preferred reaction temperature is in the range of 0° to 50° C. The reaction time depends upon the selected reaction temperature and hence the reaction is conducted for a sufficient time to permit the reaction to go to completion.

After the dehydrating condensation reaction is completed, the alkali treatment is usually carried out by the addition of a base, e.g., aqueous potassium hydroxide or sodium hydroxide solution to adjust the pH to an alkali value, e.g., 9 to 12. The treatment can be conducted in the temperature range of 0° to 100° C. The alkali treatment may be conducted in the presence of an organic solvent other than water, for example, benzene or toluene.

The benzoic acid derivative represented by Formula (II) can be prepared by reacting aminophenols, for example, 3-N-cyclohexyl-N-n-butylaminophenol, 3-N-cyclohexyl-N-isobutylaminophenol or 3-N-n-butyl-N-isobutylaminophenol, with phthalic anhydride in the absence or presence of a solvent such as benzene, toluene, xylene or trichloroethylene. A Lewis acid, such as zinc chloride, may also be added to the reaction.

Preferred examples of the diphenylamine derivatives represented by Formula (III) include compounds wherein $R_3$ is a lower alkyl group such as methyl or ethyl. A particularly preferred diphenylamine derivative is 4-methoxy-2-methyldiphenylamine, i.e., wherein $R_3$ is methyl.

The fluoran compounds of the present invention prepared by the above process can be obtained in a crystalline form which has a specific X-ray diffraction diagram by dissolving the desired product in an organic solvent and precipitating in the form of crystals.

The crystalline form of a fluoran compound in the invention can be obtained by precipitating the product prepared by the above described reaction as crystals from a solution thereof in an aromatic hydrocarbon solvent such as benzene, an alcohol solvent such as methanol, ethanol, isopropanol and n-butanol, a polar solvent such as acetonitrile and dimethylformamide, or a mixture of these solvents, and isolating the precipitated crystals.

A frequently employed method for precipitating the crystalline form thereof is to dissolve the fluoran compound completely in the solvent and then cool the solution. The mixture of the fluoran compound and the solvent may also be heated, if necessary, in the range of room temperature to the boiling point of the solvent in order to completely dissolve the fluoran compound. After dissolving completely, the resulting solution is then cooled with stirring or on standing to precipitate the crystalline form of the compound.

Isolation of the precipitated crystal requires no specific procedure and can be suitably carried out by known method such as filtration.

The crystalline solvated adducts of the fluoran compounds of the present invention, e.g., toluene adducts, can be obtained by using a solvent which forms an adduct therewith, e.g., toluene, as the solvent for precipitating the crystalline form of the compound.

For example, a crystalline toluene adduct of a fluoran compound of the present invention can be prepared by precipitating the fluoran compound from a toluene-containing solvent.

Practical examples of toluene-containing solvents include toluene and a solvent mixture of toluene with one or more other solvents, for example, alcohols such as methanol and isopropanol, acetonitrile, and hydrocarbons such as n-hexane and benzene. The toluene content in the solvent mixture is generally 2% by weight or more, preferably 5% by weight or more.

A method for precipitating the toluene adduct from a toluene-containing solvent is to dissolve the fluoran compound in toluene or the solvent mixture of toluene with other solvents and to precipitate the crystalline toluene adduct by cooling the resultant solution to a temperature from 100° to −30° C., preferably from 80° to −5° C., with stirring or on standing. Additionally or alternatively, another solvent in which the adduct is less soluble can be added to a toluene solution of the fluoran compound to precipitate the crystalline adduct.

The crystalline forms of the fluoran compounds of the present invention and the crystalline toluene adducts thereof will hereinafter be illustrated in detail.

The mole ratio of the fluoran compound to toluene in the crystalline toluene adduct of the fluoran compound of the invention and X-ray diffraction diagrams of crystal powder are as described below.

The mole ratio of the fluoran compound to toluene was determined by elementary analysis and ¹H-NMR spectrum analysis.

In the crystalline toluene adducts of the fluoran compound of Formula (I-1), the molar ratio of the fluoran compound to the toluene is from 3:1.5 to 3:2.5.

Figure 1:
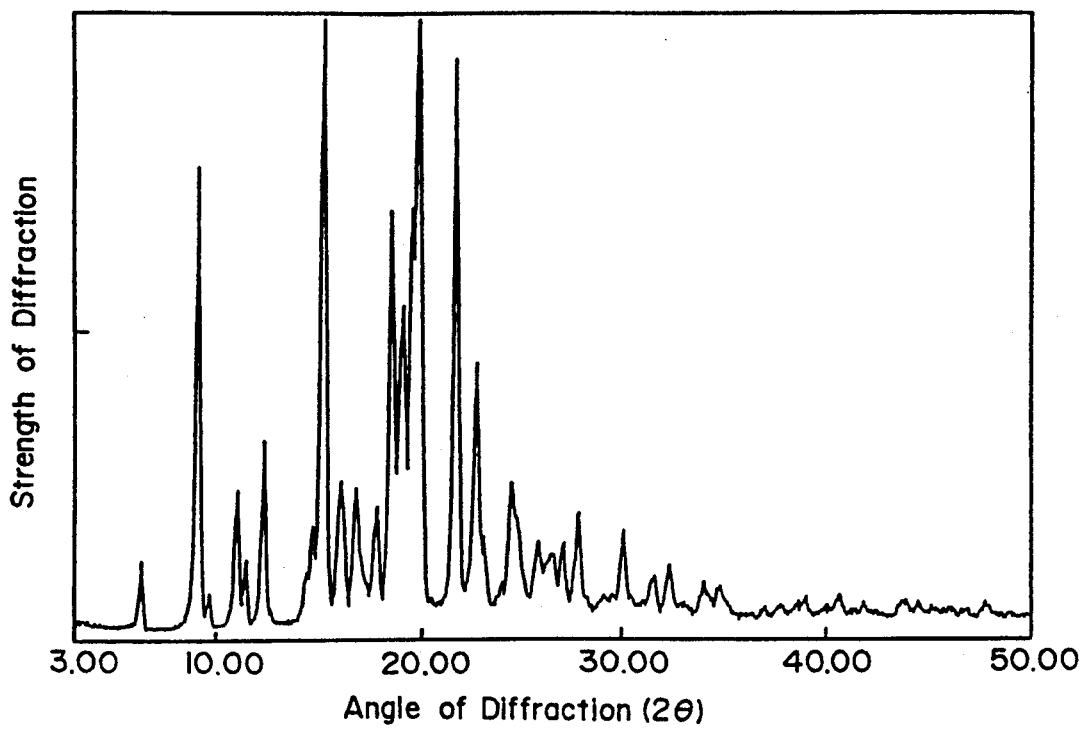
FIG. 1 is an X-ray diffraction diagram of a Type I crystal of the compound represented by Formula (I-1)

FIG. 1 illustrates an X-ray diffraction diagram by Cu-Kα beams on a powder of the crystalline form of the fluoran compound of Formula (I-1) in non-solvated form (hereinafter referred to as Type I crystal).

Figure 2:
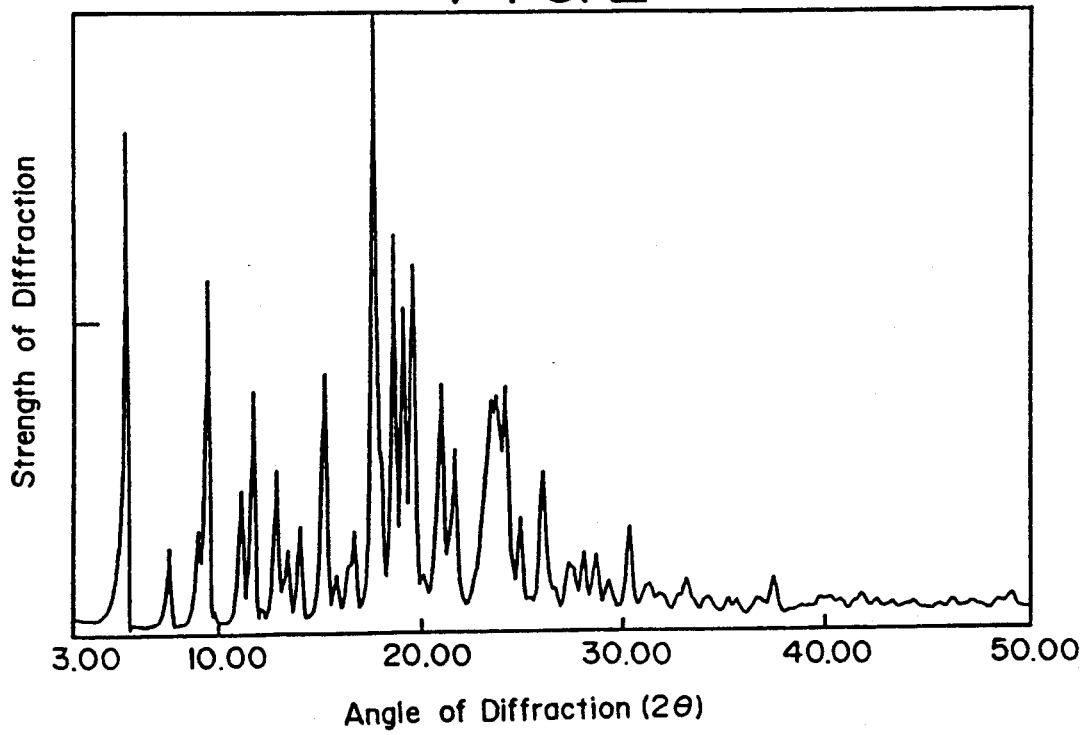
FIG. 2 is an X-ray diffraction diagram of a Type II crystal of the crystalline toluene adduct of the compound represented by Formula (I-1)

FIG. 2 illustrates an X-ray diffraction diagram of a powder of a crystalline toluene adduct of the fluoran compound of formula (I-1) (hereinafter referred to as Type II crystal).

Type I crystals exhibit high peaks at the diffraction angle (2θ) of 9.2°, 15.2°, 18.5°, 19.5°, 19.9° and 21.8°, and relatively high peaks at 19.1° and 22.8° in the X-ray diffraction diagram by Cu-Kα beams as illustrated in FIG. 1. Type II crystals exhibit high peaks at the diffraction angle (2θ) of 5.5°, 9.5°, 17.7°, 18.7°, 19.1° and 19.6°, and relatively high peaks at 11.8°, 15.3°, 21.0°, 23.4°, 23.7° and 24.2° in the X-ray diffraction diagram by Cu-Kα beams as illustrated in FIG. 2. (Errors of about ±0.2° can be permitted in the indication of diffraction angle.)

Type I crystals have a melting point of 186° to 189° C., and Type II crystals have a melting point of 124° to 128° C.

The characteristics of these X-ray diffraction diagrams and the difference in the melting points indicate that Type I crystals and Type II crystals are distinctly different crystal forms.

In the crystalline toluene adducts of the fluoran compound of formula (I-2), molar ratio of the fluoran compound to the toluene is from 4:2.5 to 4:3.5 moles.

Figure 3:
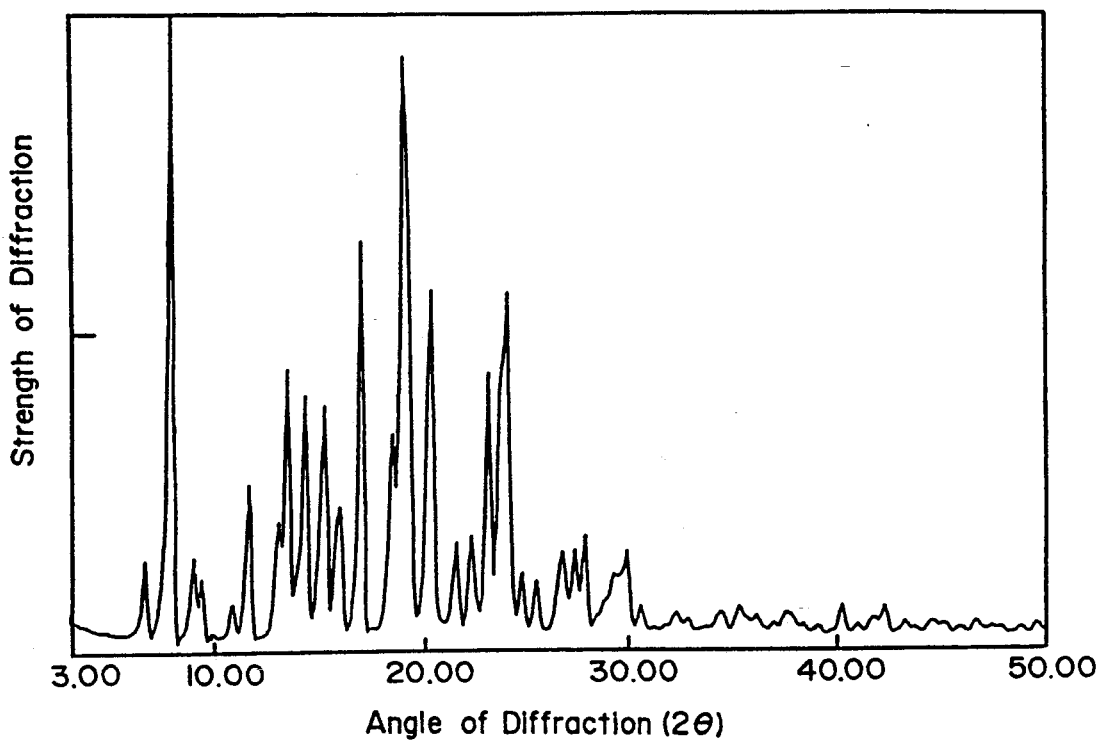
FIG. 3 is an X-ray diffraction diagram of a Type III crystal of the compound represented by Formula (I-2)

FIG. 3 illustrates a X-ray diffraction diagram of the crystalline form of the fluoran compound of Formula (I-2) which is not solvated by a solvent such as toluene (hereinafter referred to as Type III crystal).

Figure 4:
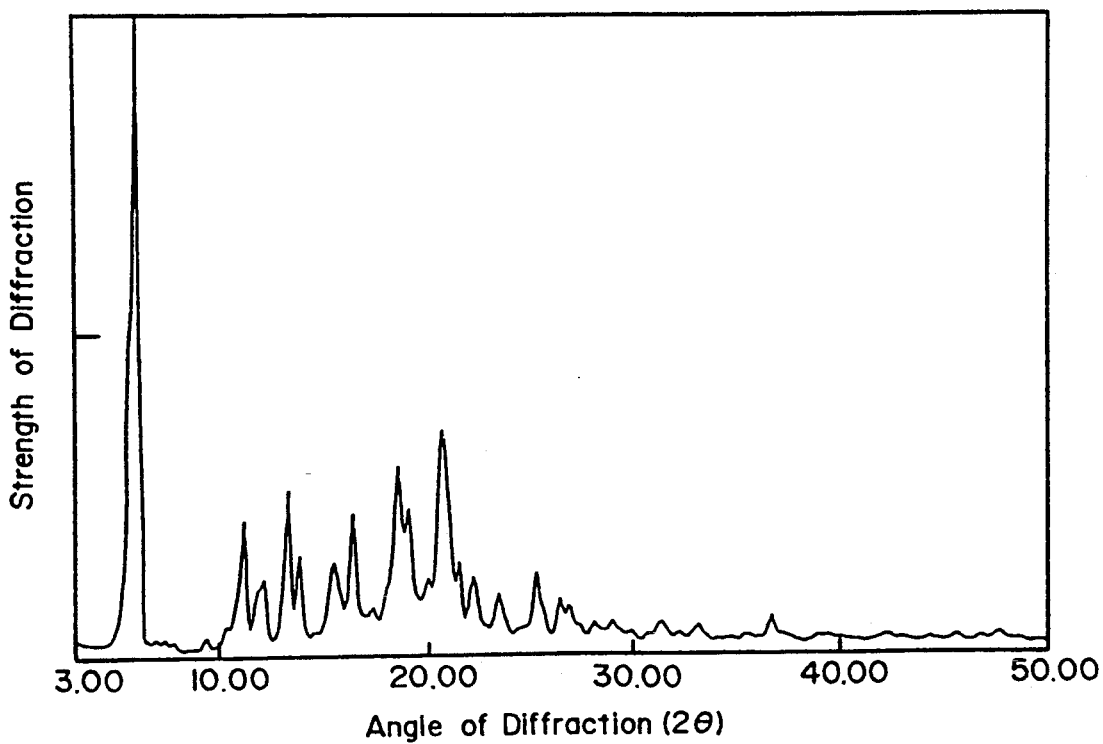
FIG. 4 is an X-ray diffraction diagram of a Type IV crystal of the crystalline toluene adduct of the compound represented by Formula (I-2)

FIG. 4 illustrates a X-ray diffraction diagram of a crystalline toluene adduct of the fluoran compound of Formula (I-2) (hereinafter referred to as Type IV crystal).

Type III crystals exhibit high peaks at the diffraction angle (2θ) of 7.9° and 19.0°, and relatively high peaks at 17.0°, 20.3° and 24.1° in the X-ray diffraction diagram by Cu-Kα beams as illustrated in FIG. 3. Type IV crystals exhibit a high peak at the diffraction angle (2θ) of 6.0° and relatively high peaks at 11.2°, 13.3°, 16.4°, 18.5°, 19.0° and 20.6° in the X-ray diffraction diagram by Cu-Kα beams as illustrated in FIG. 4.

Type III crystals have a melting point of 175° to 177° C. and Type IV crystal has melting point of 123° to 126° C.

The characteristics of these X-ray diffraction diagrams and the difference in the melting points indicate that Type III crystals and Type IV crystals are definitely different crystal forms.

Further, the crystalline toluene adducts of the fluoran compound of Formula (I-3) exist as two different crystal forms. These two crystalline toluene adducts have a molar ratio of fluoran compound to toluene of 4:2.5 and 4:3.5, respectively.

Figure 5:
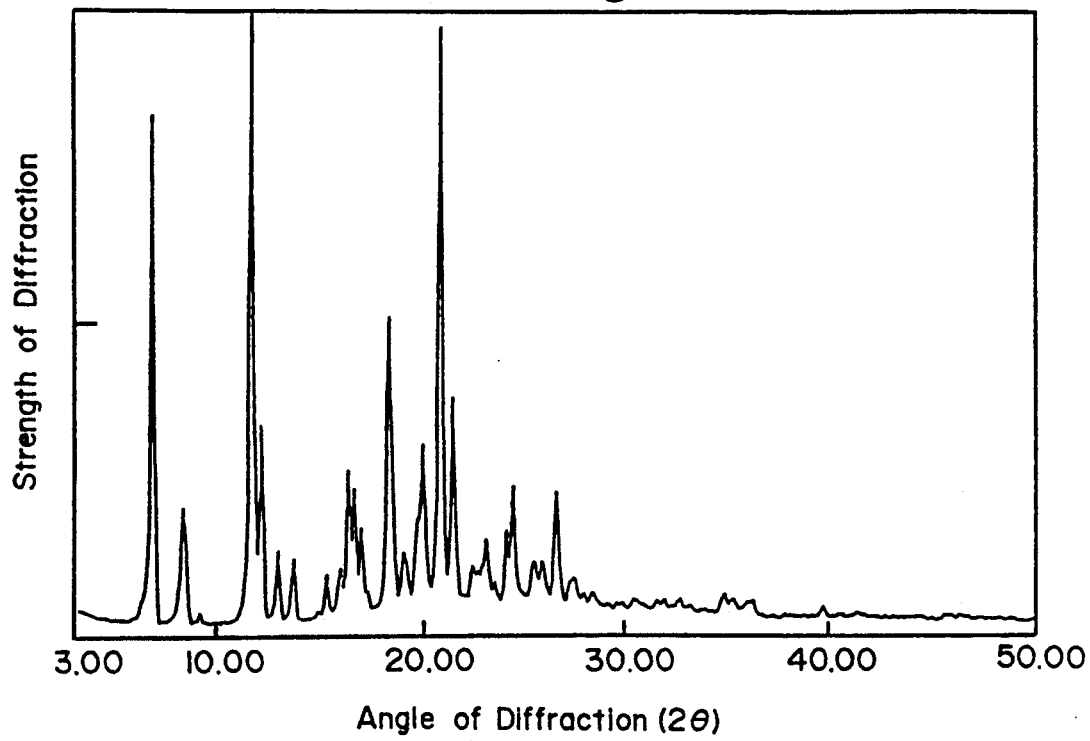
FIG. 5 is an X-ray diffraction diagram of a Type V crystal of the compound represented by Formula (I-3)

FIG. 5 illustrates an X-ray diffraction diagram of the crystal of fluoran compound of Formula (I-3) which is not solvated (hereinafter referred to as Type V crystal).

Figure 6:
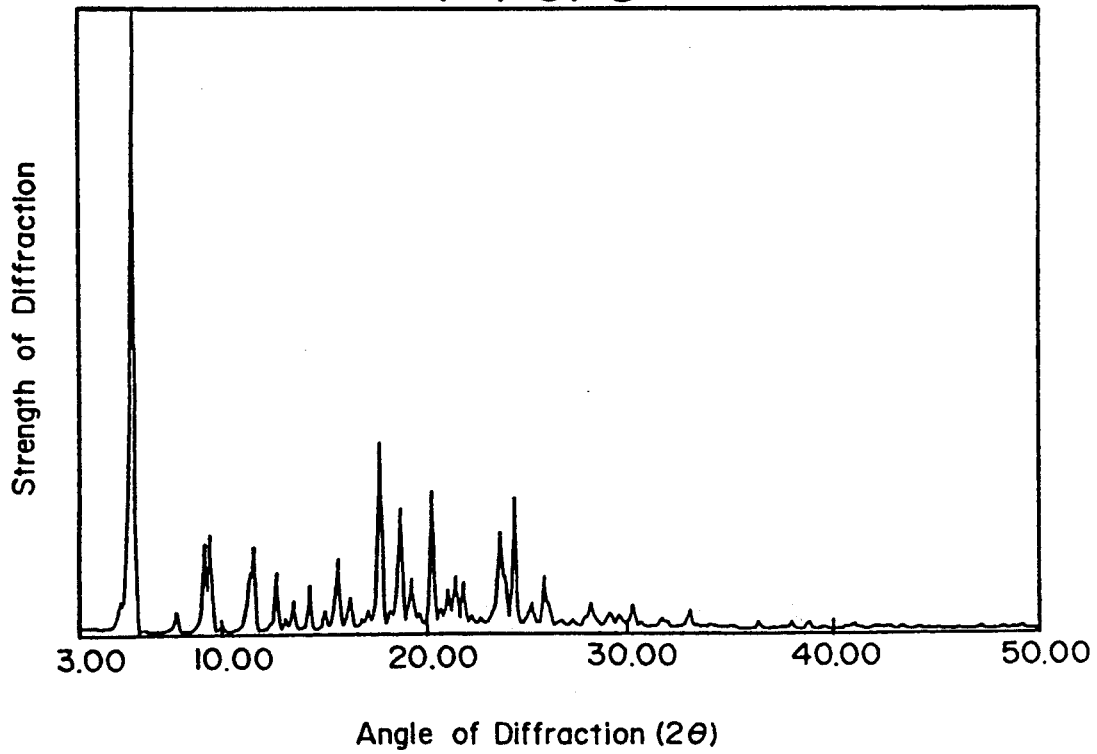
FIG. 6 is an X-ray diffraction diagram of a Type VI crystal of a crystalline toluene adduct of the compound represented by Formula (I-3)
Figure 7:
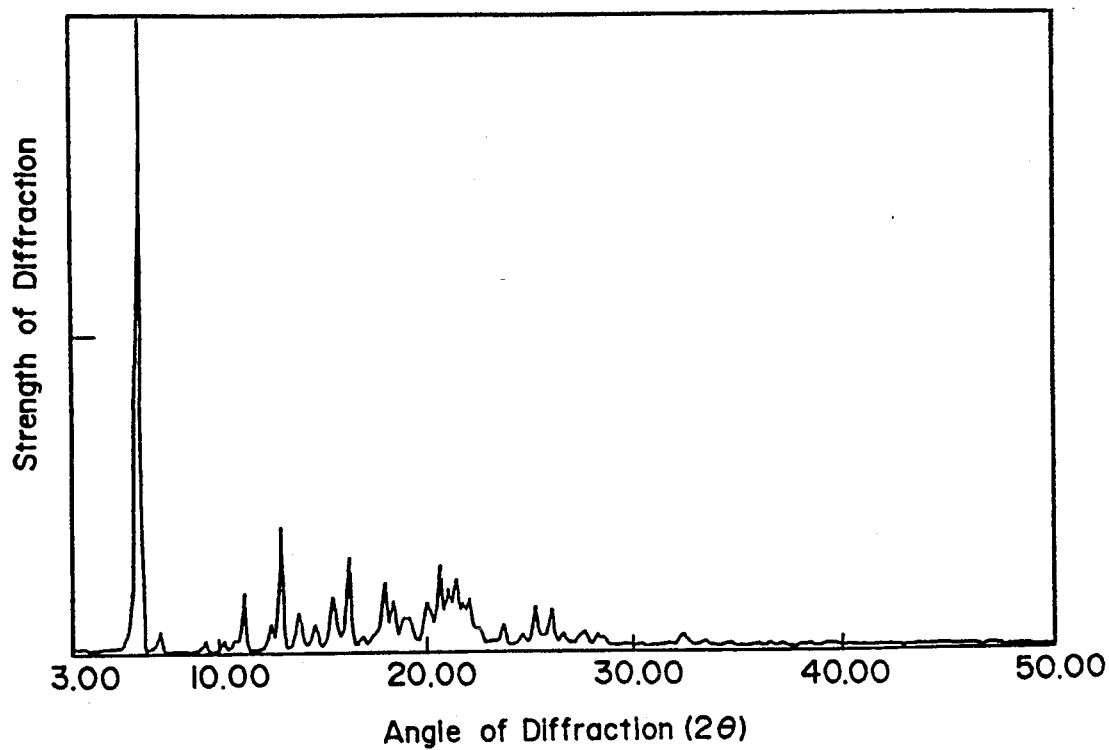
FIG. 7 is an X-ray diffraction diagram of a Type VII crystal of another crystalline toluene adduct of the compound represented by Formula (I-3).

FIG. 6 and FIG. 7 illustrate X-ray diffraction diagrams of the two kinds of crystalline toluene adducts of the compound of Formula (I-3) (hereinafter referred to as Type VI crystal and Type VII crystal, respectively).

Type V crystals exhibit high peaks at the diffraction angle (2θ) of 6.7°, 11.6° and 20.7°, and relatively high peaks at 12.1°, 18.2° and 21.3° in the X-ray diffraction diagram by Cu-Kα beams as illustrated in FIG. 5.

Type VI crystals exhibit a high peak at the diffraction angle (2θ) of 5.7° and relatively high peaks at 17.8°, 18.7°, 20.3° and 24.4° in the X-ray diffraction diagram by Cu-Kα beams as illustrated in FIG. 6

Type VII crystals exhibit a high peak at 6.3° and relatively high peaks at 13.2°, 16.4° and 20.6° in the X-ray diffraction diagram by Cu-Kα beams as illustrated in FIG. 7.

Type V crystals have a melting point of 147° to 149° C., Type VI crystals have a melting point of 116° to 119° C., and Type VII crystal have melting point of 95° to 98° C.

The characteristics of these X-ray diffraction diagrams and the difference int h melting point sindicate that Type V crystal, Type VI crystal and Type VII crystals are definitely different crystal forms.

The fluoran compounds of Formula (I), the crystalline forms thereof, and the crystalline toluene adducts thereof can provide high solubility in capsule oil, an important property which is highly desired for the chromogenic compound of pressure-sensitive recording material, and provides excellent weather resistance developed color image.

For example, the solubility of from Type I to Type VII crystals described above in commercial capsule oils were compared with known fluoran compounds having the formulas (A), (B), (C), (D) and (E). respectively. The results are shown in Table 1.

TABLE 1

| capsule oil | SAS-296 | KMC-113 | SAS-296 80% IP 20% |
|---|---|---|---|
| Type I crystal | ○ | ○ | ○ |
| Type II crystal | ○ | ○ | ○ |
| Type III crystal | ○ | ○ | ○ |
| Type IV crystal | ○ | ○ | ○ |
| Type V crystal | ○ | ○ | ○ |
| Type VI crystal | ○ | ○ | ○ |
| Type VII crystal | ○ | ○ | ○ |
| Compound of formula (A) | X | X | X |
| Compound of formula (B) | X | X | X |
| Compound of formula (C) | X | X | X |
| Compound of formula (D) | X | X | X |
| Compound of formula (E) | X | X | X |

The method for determining the solubility is as follows. Each crystal or compound is dissolved by heating at a concentration of 10% by weight in the three capsule oils, respectively. After standing at 5° C. for a week, the capsule oil is examined for precipitation of crystals. In Table ; ○ means that no crystals are precipitated and x means that precipitation of crystals is observed.

SAS-296 is a capsule oil produced by Nippon Petrochemical Co., Ltd. and KMC-113 is a capsule oil produced by Kureha Chemical Industry Co., Ltd. IP is isoparaffine. The compound of Formula (A) cannot be completely dissolved even in hot KMC-113.

As clearly illustrated in Table 1, the fluoran compound represented by Formula (I), these compounds in crystalline form and the crystalline toluene adducts of the fluoran compounds all have high solubility in each capsule oil in cotrdistinction to the fluoran compounds of the formulas (A), (B), (C), (D) and (E).

These results mean that crystal precipitation does not occur during storage in the capsule oil in the preparation of the pressure-sensitive recording material, and that crystal precipitation in the microcapsules is not liable to occur after preparation of microcapsules. Such good solubility in the capsule oils is an important characteristic of the fluoran compounds of the present invention, including the crystalline forms thereof and the crystalline toluene adducts thereof very good solubility in a mixed oil of SAS 296 and IP-oil, in particular, means that cheaper capsule oil can also be employed, which circumstances are advantageous in economy and industry.

The fluoran compounds of the invention, including the crystalline forms thereof and the crystalline toluene adducts thereof can provide a heat-sensitive recording paper which is free from soiling and has high whiteness. The recording paper thus obtained can develop color more quickly at lower temperatures, compared with the compounds of formulas (A), (B), (C), (D) and (E). Hence the fluoran compounds of the present invention have extremely excellent properties in view of the present demand for high speed and high density recording materials.

The recording materials of the present invention are pressure-sensitive recording material or heat-sensitive recording material which comprise a fluoran compound of the present invention, e.g., a crystalline form thereof or a crystalline solvent e.g. toluene, adduct thereof.

The chromogenic compound employed therein can be a single fluoran compound or a mixture of fluoran compounds of the invention, e.g., as a crystalline form thereof and/or a crystalline solvent, e.g., toluene, adduct thereof. Further, in order to adjust the developed hue, other chromogenic materials such as triphenylmethanlactones, fluorans and spiropiranes can also be added depending upon the demand.

When preparing pressure-sensitive recording material, a fluoran compound of the invention, e.g., a crystalline form thereof or a crystalline toluene adduct thereof, is dissolved in the selected solvent, i.e., capsule oil. The solvent which is generally used in the field of pressure sensitive recording includes single solvents and mixture thereof, for example, alkylbenzenes such as n-dodecylbenzene, alkylbiphenyls such as triethylbiphenyl and diisopropylbiphenyl, hydrogenated terphenyls, alkylnaphthalenes such as diisopropylnaphthalene, diarylethanes such as phenylxylylethane and styrenated ethylbenzene, and chlorinated paraffins. The resulting solution is sealed by a coacervation method or an interfacial polymerization method into microcapsules having an external wall comprised of gelatin, melaminealdehyde resin, urea-aldehyde resin, polyurethane, polyurea, polyamide or the like. Aqueous dispersion of the microcapsules is mixed with a suitable binder, such as starch paste and latex, and applied to a suitable substrate such as paper, plastic sheet or resin coated paper. The coated back sheet for pressure-sensitive recording is thus obtained.

The micro dispersion thus obtained can, of course, be used to Produce so-called middle-sheets wherein the microcapsule dispersion is applied to one side of a substrate and a coating liquid primarily comprising a developer is applied to the other side of the substrate, and to produce so-called self contained sheets wherein both the microcapsules and the developer are present on the same side of a substrate.

The self contained sheet is prepared by applying a coating liquid comprising the microcapsules and the developer to one side of the substrate or by applying a microcapsules dispersion to one side of the substrate and then applying a coating liquid of the developer on the coated layer of the microcapsules.

Exemplary developer suitable for use in the pressure-sensitive recording material includes copolymers of salicylic acid, phenols and aldehydes such as form aldehyde; alkyl, aryl or aralkyl substituted salicylic acid such as 3,5-di-α-methylbenzylsalicylic acid; polycondensate of substituted salicylic acid and styrene; alkylphenols such as octylphenol; phenol aldehyde resin, such as p-phenylphenol novolak resin; metal salts of these compounds such as zinc, magnesium, aluminum, calcium, tin and nickel salts; and activated clays.

When preparing a heat-sensitive recording material of the invention, a fluoran compound of the invention, e.g., a crystalline form thereof or a crystalline toluene adduct thereof is pulverized in water to form an aqueous dispersion. The dispersion is mixed with an aqueous dispersion of pulverized developer, and binder is added to the thus obtained mixture.

Representative examples of developers which are suitable for use in the heat sensitive recording material include bisphenol A, halogenated bisphenol A, alkylated bisphenol A, dihydroxydiphenyl sulfone, halogenated dihydroxydiphenyl sulfone, alkylated dihydroxydiphenyl sulfone, hydroxybenzoic acid esters, hydroquinone monoethers and other phenol derivatives; organic developers such as salicylic acid derivatives, salicylamide derivatives, urea derivatives, and thiourea derivatives; and inorganic developers such as acid clay, attapulgite, activated clay, aluminum chloride and zinc bromide.

Exemplary binder used for the heat-sensitive recording material includes polyvinyl alcohol, modified polyvinyl alcohol, methylcellulose, hydroxyethylcellulose, carboxymethylcellulose, gum arabic, salt of styrene-maleic anhydride copolymer, and isobutyleneacrylic acid-maleic anhydride copolymer.

Other additives can also be employed. Exemplary additives include fillers such as talc, kaolin and calcium carbonate, and if necessary, may also include sensitizers such as higher fatty acid amides, aromatic carboxylic acid esters, aromatic sulfonic acid esters, aromatic ethers, aromatic substituted aliphatic ethers, aromatic hydrocarbons, aromatic substituted aliphatic hydrocarbons and other generally known sensitizers for the heat-sensitive recording material; UV-absorbers; and defoamers.

The coating liquid obtained by the addition of the above additives can be applied to a suitable substrate such as paper, plastic sheet and resin coated paper and used as the heat-sensitive recording material. The heat-sensitive recording system of the invention can of course be used in a solvent system without any problem in place of the above aqueous dispersion system. The system of the invention can also be employed for other enduse applications using chromogenic materials, for example, a temperature-indicating material.

The color density characteristics dependent upon the temperature change were measured on the heat-sensitive recording material of the present invention, that is, a heat-sensitive recording paper obtained by using the crystalline form and the crystalline toluene adduct of a fluoran compound represented by the formula (I) as the chromogenic compound and using bisphenol A as the developer. The results are illustrated in FIGS. 8, 9 and 10. Color density was measured with a Macbeth reflection densitometer (Model; TR-524). Larger values indicate higher density of developed color.

FIG. 8 illustrates the color density characteristics depending upon temperature change for Type I and Type II crystals of the invention and reference compounds of Formulas (A), (B) and (C), FIG. 9 illustrates the same relationship on Type III and Type IV crystals of the invention and a reference compound of Formula (D), and FIG. 10 illustrates the same relationship on Type V, Type VI and Type VII crystals of the present invention and a reference compound of Formula (E), respectively.

FIG. 8 illustrates that Type I and Type II crystals of the invention have the excellent characteristic of developing color more quickly at lower temperatures as compared with the compounds of Formulas (A), (B) and (C). FIG. 9 illustrates that Type III and Type IV crystals of the invention have the excellent characteristic of developing color more quickly at lower temperatures as compared with the compounds of Formulas (C) and (D). FIG. 10 illustrates that Type V, Type VI and Type VII crystals of the invention have the excellent characteristic of developing color more quickly at lower temperatures as compared with the compounds of Formulas (A), (B) and (D).

In order to develop color at lower temperatures, a sensitizer which is a heat-fusible substance having a relatively low melting point of about 100° C. is commonly used in addition to the chromogenic compound and the developer. On the other hand, a fluoran compound represented by the formula (I) of the invention, e.g., a crystalline form thereof or a crystalline toluene adduct thereof, has the remarkable advantage that color development can be quickly achieved at lower temperature in the absence of the sensitizer or in the presence of a smaller amount of the sensitizer as compared to using a compound of Formulas (A), (B), (C), (D) or (E).

The fluoran compounds of Formula (I) differs from the fluoran compounds of Formulas (A), (B), (C), (D) and (E) only in the substituent on the amino group at the 3 position of the fluoran structure. For example, the compounds of Formula (I-1) and Formula (I-2) differ from the methylamino substituted compound of 3 position of Formula (C) or the isoamylamino substituted compound of formula (D) by an n butylamino or an isobutylamino group, respectively. Similarly, the compound of Formula (I-3) differs from the compound of Formula (B) by one of the butyl groups on the amino group at the 3 position being isobutyl instead of n-butyl. Although these differences in chemical structure are small, as mentioned above, the fluoran compounds of the present invention have extremely outstanding characteristics as the chromogenic compound, for example, solubility in capsule oils and heat-sensitive color developing characteristics.

The present invention will hereinafter be illustrated further in detail by way of examples. However, it is to be understood that the invention is not intended to be limited to the specific embodiments.

EXAMPLE 1

[Preparation of Type I crystals of the fluoran compound of formula (I-1)]

After dissolving 20 g of 2-(4'-N-cyclohexyl-N-n-butylamino-2'-hydroxybenzoyl)benzoic acid, i.e., the compound of Formula (II-1), in 100 ml of concentrated sulfuric acid at 10° C., 11 g of 4-methoxy-2-methyldiphenylamine, i.e., the compound of Formula (III) wherein $R_3$ is methyl, was added at the same temperature and stirred at 10° to 25° C. for 48 hours. The reaction mixture was poured into 600 ml of ice water. The separated solid was collected, washed with water and added to 500 ml of a 10% aqueous sodium hydroxide solution, and stirred at 60° to 70° C. for 2 hours. Thereafter the solid was filtered, washed with water and further washed with 100 ml of isopropanol.

The resulting solid was recrystallized twice with n-butanol to obtain 20 g of the desired 3-N-cyclohexyl-N-n-butylamino-6-methyl-7-anilinofluoran as almost colorless crystals. Yield was 67% and melting point was 186° to 189° C.

A toluene solution of the compound thus obtained was colorless and transparent. A reddish black color quickly developed on silica gel. The compound had a maximum absorption at a wave length of 455 nm and 594 nm in a 95% aqueous acetic acid solution. An X-ray diffraction diagram of the powder of these crystals is illustrated in FIG. 1.

EXAMPLE 2

[Preparation of Type II crystals of a crystalline toluene adduct of the fluoran compound of Formula (I-1)]

After dissolving 200 g of 2-(4'-N-cyclohexyl-N-n-butylamino-2'-hydroxybenzoyl)benzoic acid in 600 ml of concentrated sulfuric acid at 10° C., 110 g of 4-methoxy-2-methyldiphenylamine was added at the same temperature and stirred at 10° to 25° C. for 48 hours.

The reaction mixture was poured into 6000 ml of ice water. The separated solid was collected, washed with water and added to 1000 ml of a 20% aqueous sodium hydroxide solution. A further 1000 ml of toluene was added to the resultant mixture and stirred at 60° to 70° C. for 2 hours.

The toluene layer was separated and washed with warm water until the water became neutral after washing. The toluene solution thus obtained was concentrated at 40° C. under reduced pressure. The separated crystals were filtered, washed with a small amount of toluene, further washed with methanol and dried at 40° C. for 18 hours to obtain 250 g of toluene adduct of 3-N-cyclohexyl-N-n-butylamino-6-methyl-7-anilino-fluoran as almost colorless crystals. Melting point was 124° to 128° C.

Elementary analysis (3·$C_{37}H_{38}O_3N_2$:2·$C_7H_8$)

|  | C | H | N |
|---|---|---|---|
| Calculated (%) | 80.70 | 7.04 | 4.52 |
| Found (%) | 80.83 | 7.02 | 4.75 |

A toluene solution of the compound thus obtained was colorless and transparent. A reddish black color quickly developed on silica gel. The compound had a maximum absorption at a wave length of 455 nm and 594 nm in a 95% aqueous acetic acid solution. An X-ray diffraction diagram of the powder is illustrated in FIG. 2.

EXAMPLE 3

[preparation of Type II crystals of a crystalline toluene adduct of the fluoran compound of Formula (I-1)]

After dissolving 20 g of 2-(4'-N-cyclohexyl-N-n-butylamino-2'-hydroxybenzoyl)benzoic acid in 100 ml of concentrated sulfuric acid at 10° C., 11 g of 4-methoxy-2-methyldiphenylamine was added at the same temperature and stirred at 10° to 25° C. for 48 hours.

The reaction mixture was poured into 600 ml of ice water. The separated solid was collected, washed with water and added to 500 ml of a 10% aqueous sodium hydroxide solution. A further 300 ml of toluene was added to the resultant mixture and stirred at 60° to 70° C. for 2 hours.

The toluene layer was separated and washed with warm water until the water became neutral after washing. Thereafter 280 ml of toluene was distilled off from the toluene solution at 50° C. under reduced pressure. The residual viscous oil was mixed with 300 ml of methanol to precipitate crystals. The desired toluene adduct of 3 N cyclohexyl-N-n-butylamino-6-methyl-7-anilinofluoran thus obtained was 22 g. The adduct was almost colorless crystals and had a melting point of 124° to 128° C.

EXAMPLE 4

[Preparation of Type I crystals from Type II crystals]

After dissolving 20 g of Type II crystals of Example 2 in 100 ml of acetonitrile, the solution obtained was cooled to the room temperature. The crystals which separated were filtered to obtain 17 g of Type I crystals. Melting point was 186° to 189° C.

EXAMPLE 5

[Preparation of Type III crystals of the fluoran compound of Formula (I-2)]

After dissolving 100 g of 2-(4'-N-cyclohexyl-N-isobutylamino-2'-hydroxybenzoyl)benzoic acid in 300 ml of concentrated sulfuric acid at 10° C., 53 g of 4-methoxy-2-methyldiphenylamine was added at the same temperature and stirred at 10° to 25° C. for 48 hours.

The reaction mixture was poured into 1500 ml of ice water the separated solid was collected, washed with water and added to 1000 ml of a 10% aqueous sodium hydroxide solution. A further 800 ml of toluene was added to the resultant mixture and stirred at 60° to 70° C for 2 hours. The toluene layer was separated and washed with warm water until the water became neutral after washing. The toluene solution thus obtained was concentrated to 200 ml by distilling off toluene at 50° C. under reduced pressure and allowed to cool to room temperature.

The precipitated crystals were filtered, slurried with 1000 ml of methanol and washed with 500 ml of methanol to obtain 88 g of 3-N-cyclohexyl-N-isobutylamino-6-methyl-7-anilinofluoran. Yield was 62% and melting point was 175° to 177° C. A toluene solution of the compound was colorless and transparent. A reddish black color quickly developed on silica gel. The compound had a maximum absorption at a wave length of 455 nm and 595 nm in a 95% aqueous acetic acid solution. The X-ray diffraction diagram of the powder is illustrated in FIG. 3.

EXAMPLE 6

[Preparation of Type IV crystals of crystalline toluene adduct of the fluoran compound of Formula (I-2)]

After dissolving 100 g of 2-(4'-N-cyclohexyl-N-isobutylamino-2'-hydroxybenzoyl)benzoic acid in 300 ml of concentrated sulfuric acid at 10° C., 53 g of 4-methoxy-2-methyldiphenylamine was added at the same temperature and stirred at 10° to 25° C. for 48 hours.

The reaction mixture was poured into 1500 ml of ice water. The separated solid was collected, washed with water and added to 1000 ml of a 10% aqueous sodium hydroxide solution. A further 800 ml of toluene was added to the resultant mixture and stirred at 60° to 70° C. for 2 hours.

The toluene layer was separated and washed with warm water until the water became neutral after washing. Thereafter the toluene solution was concentrated to 200 ml at 50° C. under reduced pressure. After allowed to cool to room temperature, the crystals which separated were filtered, washed with a small amount of toluene, and dried to obtain 100 g of toluene adduct of 3-N-cyclohexyl-N-iso-butylamino-6-methyl-7-anilinofluoran as almost colorless crystals. Melting point was 123° to 126° C.

Elementary analysis (4·C$_{17}$H$_{38}$O$_3$N$_2$:3·C$_7$H$_8$)

|  | C | H | N |
|---|---|---|---|
| Calculated (%) | 80.83 | 7.06 | 4.46 |
| Found (%) | 80.75 | 7.07 | 4.51 |

A toluene solution of the compound thus obtained was colorless and transparent. A reddish black color was quickly developed on silica gel. The compound had a maximum absorption at a wave length of 455 nm and 595 nm in a 95% aqueous acetic acid solution. The X-ray diffraction diagram of the powder is illustrated in FIG. 4.

EXAMPLE 7

[Preparation of Type III crystals from Type IV crystals]

After dissolving 20 g of Type IV crystals, prepared as described in Example 6, in 100 ml of methanol by heating, the solution was cooled to room temperature. Separated crystals were filtered to obtain 15 g of Type III crystals. Melting point was 175 to 177° C.

EXAMPLE 8

[Preparation of Type V crystals of the fluoran compound of Formula (I-3)]

After dissolving 29.5 g of 2-(4'-N-n-butyl-N-isobutylamino-2'-hydroxybenzoyl)benzoic acid in 100 ml of concentrated sulfuric acid at 10° C., 17 g of 4-methoxy-2-methyldiphenylamine was added at the same temperature and the mixture was stirred at 10° to 25° C. for 48 hours.

The reaction mixture was poured into 600 ml of ice water. The separated solid was collected, washed with water and added to 500 ml of a 10% aqueous sodium hydroxide solution. The mixture was stirred at 60° to 70° C. for 2 hours. The solid was filtered, washed with water, washed with 100 ml of isopropanol and further recrystalized twice from isopropanol to obtain 26 g of 3-N-n-butyl-N-isobutylamino-6-methyl-7-anilinofluoran as almost colorless crystals. Yield was 62%. Melting point was 147°–149°.

A toluene solution of the compound thus obtained was colorless and transparent. A reddish black color was quickly developed on silica gel. The compound had a maximum absorption at a wave length of 452 nm and 594 nm in a 95% aqueous acetic acid solution. The X-ray diffraction diagram of the powder is illustrated in FIG. 5.

EXAMPLE 9

[Preparation of Type VI crystals of crystalline toluene adduct of the fluoran compound of Formula (I-3)]

After dissolving 29.5 g of 2-(4'-N-n-butyl-N-isobutylamino-2'-hydroxybenzoyl)benzoic acid in 100 ml of concentrated sulfuric acid at 10° C., 17 g of 4-methoxy-2-methyldiphenylamine was added at the same temperature and the mixture was stirred at 10° to 25° C. for 48 hours.

The reaction mixture was poured into 600 ml of ice water. The separated solid was collected, washed with water and added to 500 ml of a 10% aqueous sodium hydroxide solution. A further 300 ml of toluene was added to the resultant mixture, which was then stirred at 60° to 70° C. for 2 hours.

The toluene layer was separated and washed with warm water until the water becomes neutral after washing. Thereafter 280 ml of toluene was distilled off at 50° C. under reduced pressure. The residual viscous oil was crystallized by mixing with 300 ml of methanol to obtain 35.3 g of toluene adduct of 3-N-n-butyl-N-isobutylamino-6-methyl-7-anilinofluoran as almost colorless crystals. Melting point was 116° to 119° C.

Elementary analysis ($3 \cdot C_{35}H_{36}O_3N_2 \cdot 2 \cdot C_7H_8$)

|  | C | H | N |
|---|---|---|---|
| Calculated (%) | 80.19 | 7.01 | 4.72 |
| Found (%) | 79.96 | 6.93 | 4.87 |

A toluene solution of the compound thus obtained was colorless and transparent. A reddish black color was quickly developed on silica gel. The compound had a maximum absorption at a wave length of 452 nm and 594 nm in a 95% aqueous acetic acid solution. The X-ray diffraction diagram of the powder is illustrated in FIG. 6.

EXAMPLE 10

[Preparation of Type VII crystals of crystalline toluene adduct of the fluoran compound of Formula (I-3)]

After dissolving 100 g of 2-4'-N-n-butyl-N-isobutylamino-2'-hydroxybenzoyl)benzoic acid in 330 ml of concentrated sulfuric acid at 10° C., 58 g of 4-methoxy-2-methyldiphenylamine was added at the same temperature and stirred at 10° to 25° C. for 48 hours.

The reaction mixture was poured into 2000 ml of ice water. The separated solid was collected, washed with water and added to 1500 ml of a 10% aqueous sodium hydroxide solution. A further 1000 ml of toluene was added to the resultant mixture, which was then stirred at 60° to 70° C. for 2 hours.

The toluene layer was separated and washed with warm water until the water becomes neutral after washing. Thereafter the toluene layer was allowed to stand at room temperature. The precipitated crystals were filtered, washed with a small amount of toluene, further washed with methanol and dried to obtained 115 g of the toluene adduct of 3-N-n-butyl-N-iso-butylamino 6-methyl-7-anilinofluoran as almost colorless crystals. Melting point was 95 to 98° C.

Elementary analysis ($3 \cdot C_{35}H_{36}O_3N_2 \cdot 2 \cdot C_7H_8$)

|  | C | H | N |
|---|---|---|---|
| Calculated (%) | 80.19 | 7.01 | 4.72 |
| Found (%) | 80.10 | 6.97 | 4.70 |

A toluene solution of the compound thus obtained was colorless and transparent. A reddish black color was quickly developed 0n silica gel. The compound had a maximum absorption at a wave length of 452 nm and 594 nm in a 95% aqueous acetic acid solution. The X-ray diffraction diagram of the powder is illustrated in FIG. 7.

EXAMPLE 11

[Preparation of Type V crystals from Type VI crystals]

After dissolving 20 g of Type VI crystals, prepared as described in Example 9, in 180 ml of isopropanol by heating, the solution was cooled to the room temperature. Separated crystals were filtered to obtain 17 g of Type V crystals. Melting point was 147° to 149° C.

EXAMPLE 12

[Preparation of Type V crystals from Type VII crystals]

After dissolving 20 g of Type VII crystals prepared in Example 10 in 180 ml of isopropanol by heating, the solution was cooled to the room temperature. The crystals which separated were filtered to obtain 17 g of Type V crystals. Melting point was 147° to 149° C.

EXAMPLE 13

[Preparation of heat-sensitive recording paper using Type I crystals of the compound of Formula (I-1)]

A mixture of 10 g of Type I crystals of the compound represented by Formula (I-1), 5 g of 10% aqueous polyvinyl alcohol solution and 37.5 g of water was pulverized to a particle size of 3 μ using a sand mill. Separately, bisphenol A was dispersed in a similar manner to obtain a 38% dispersion of developer. Then 65.8 g of the developer dispersion thus obtained, 50.9 of the above aqueous dispersion of Type I crystals, 18.3 g of 60% aqueous precipitated calcium carbonate dispersion, 88 g of 10% aqueous polyvinyl alcohol solution and 51.9 g of water were mixed.

The thus-obtained mixture was applied on a white base paper by using a wire rod No. 10 and air-dried at the room temperature to obtain an extremely white heat-sensitive recording paper which was free from soiling. When the heat-sensitive recording paper thus obtained was heated, a slightly reddish black color was very quickly developed.

The color density characteristics of the heat-sensitive recording paper to temperature change was measured with RHODIACETA ™ (LYON, FRANCE). The results are illustrated in FIG. 8.

Color density was measured with a Macbeth reflection densitometer Model TR-524. A larger value indicates higher color density.

EXAMPLE 14

[Preparation of heat-sensitive recording paper using Type II crystals of the crystalline toluene adduct of the compound of Formula (I-1)]

A heat sensitive recording paper was prepared carrying out the same procedures as described in Example 13 except that Type II crystals of the crystalline toluene adduct of the compound of Formula (I-1) were used in place of Type crystals of the compound of Formula (I-1).

A slightly reddish black color was very quickly developed by heating the heat-sensitive recording paper thus obtained.

The color density characteristics of the heat-sensitive recording paper to temperature change was measured with RHODIACETA TM (LYON, FRANCE). The result are illustrated in FIG. 8.

EXAMPLE 15

[Preparation of heat-sensitive recording paper using Type III crystals of the compound of Formula (I-2)]

A heat-sensitive recording paper was prepared carrying out the same procedures as described in Example 13 except that Type III crystals of the compound of Formula (I-2) were used in place of Type I crystals of the compound of Formula (I-1).

A slightly reddish black color was very quickly developed by heating the heat sensitive recording paper thus obtained.

The color density characteristics of the heat-sensitive recording paper to temperature change was measured with RHODIACETA TM (LYON, FRANCE). The results are illustrated in FIG. 9.

EXAMPLE 16

[Preparation of heat-sensitive recording paper using Type IV crystals of the crystalline toluene adduct of the compound of Formula (I-2)]

A heat-sensitive recording paper was prepared carrying out the same procedures as described in Example 13 except that Type IV crystals of the crystalline toluene adduct of the compound of Formula (I-2) were used in place of Type I crystals of the compound of Formula (I-1).

A slightly reddish black color was very quickly developed by heating the heat-sensitive recording paper thus obtained.

The color density characteristics of the heat-sensitive recording paper to temperature change was measured with RHODIACETA TM (LYON, FRANCE). The results are illustrated in FIG. 9.

EXAMPLE 17

[Preparation of heat-sensitive recording paper using Type V crystals of the compound of Formula (I-3)]

A heat-sensitive recording paper was prepared carrying out the same procedures as described in Example 13 except that Type V crystals of the compound of Formula (I-3) were used in place of Type I crystals of the compound of Formula (I-1).

A slightly reddish black color was very quickly developed by heating the heat-sensitive recording paper thus obtained.

The color density characteristics of the heat-sensitive recording paper to temperature change was measured with RHODIACETA TM (LYON, FRANCE). The results are illustrated in FIG. 10.

EXAMPLE 18

[Preparation of heat-sensitive recording paper using Type VI crystals of the crystalline toluene adduct of the compound of Formula (I-3)]

A heat-sensitive recording paper was prepared carrying out the same procedures as described in Example 13 except that Type VI crystals of the crystalline toluene adduct of the compound of Formula (I-3) were used in place of Type I crystals of the compound of Formula (I-1).

A slightly reddish black color was very quickly developed by heating the heat-sensitive recording paper thus obtained.

The color density characteristics of the heat-sensitive recording paper to temperature change was measured with RHODIACETA TM (LYON, FRANCE). The result are illustrated in FIG. 10.

EXAMPLE 19

[Preparation of heat-sensitive recording paper using Type VII crystals of the Crystalline toluene adduct of the compound of Formula (I-3)]

A heat-sensitive recording paper was prepared by carrying out the same procedures as described in Example 13 except that Type VII crystals Of the crystalline toluene adduct of the compound of Formula (I-3) were used in place of Type I crystals of the compound represented by the formula (I-1).

A slightly reddish black color very quickly developed by heating the heat-sensitive recording paper thus obtained.

The color density characteristics of the heat-sensitive recording paper to temperature change was measured with RHODIACETA TM (LYON, FRANCE). The results are illustrated in FIG. 10.

COMPARATIVE EXAMPLE

Heat-sensitive recording papers were prepared carrying out the same procedures as described in Example 13 except that Type I crystals of the compound of Formula (I-1) were replaced by 3-N,N-diethylamino-6-methyl-7-anilinofluoran [compound of Formula (A)], 3-N,N-di-n-butylamino-6-methyl-7-anilinofluoran [compound of Formula (B)], 3-N-cyclohexyl-N-methylamino-6-methyl-7-anilinofluoran [compound of Formula (C)], 3-N-cyclohexyl-N-isoamylamino-6-methyl-7-anilinofluoran [compound of Formula (D), and 3-N-isobutyl-N-ethyl-6-methyl-7-anilinofluoran [compound of Formula (E)], respectively. Color density characteristics to temperature change were measured. Results are illustrated in FIGS. 8, 9 and 10.

Additionally, the surface of the heat-sensitive recording paper to which the compound of the formula (A) was applied had somewhat greyish color and greasing was observed.

EXAMPLE 20

[Preparation of pressure-sensitive recording paper using Type I crystal of the compound of Formula (I-1)]

Coated back sheet (CB) and coated front sheet (CF) were prepared by the following procedures.

A mixture of 100 g of a 10% aqueous solution of ethylenemaleic anhydride copolymer and 240 g of water was adjusted to PH 4.0 with a 10% aqueous sodium hydroxide solution and mixed with 200 g of a solution containing 5% by weight of Type I crystals of the compound of Formula (I-1) in phenylxylylethane (SAS-296; Trade Mark of a product of Nippon Petrochemical Co., Ltd.). After emulsifying the resultant mixture with a homomixer, 60 g of an aqueous methylolmelamine solution containing 50% of solid (Uramine T-30; Trade Mark of a product of Mitsui Toatsu Chemicals Inc.) was added, and stirred at 55° C. for 3 hours to obtain a microcapsule dispersion having an average particle size of 5.0 μ.

To 100 g of the microcapsule dispersion, 4.0 g of wheat starch, 20 g of 20% paste of oxidized starch and 116 g of water were added and dispersed. The dispersion thus obtained was applied on a paper having a basis weight of 40 g/m² so as to obtain a coating weight of 5 g/m² as solid, CB sheet was thus obtained.

On the other hand, in order to prepare CF sheet, the zinc salt of a substituted salicylic acid styrene copolymer was pulverized in water with a sand grinding mill in the presence of a small amount of a high molecular weight anionic surfactant to obtain an aqueous dispersion with a 40% by weight solids content. Using the aqueous dispersion, a coating compound (30% solid content) having the below described composition was prepared and applied on a woodfree paper having a basis weight of 40 g/m² so as to obtain a coating wight of 5.5 g/m². A CF sheet was thus obtained.

| Aqueous Coating Composition | Weight of solid (g) |
| --- | --- |
| Precipitated calcium carbonate | 100 |
| Developer | 20 |
| Binder (Starch) | 8 |
| (Synthetic latex) | 8 |

The microcapsule coated CB sheet and the developer coated CF sheet were overlapped so as to bring both coated surfaces into contact with each other. When pressure was applied on the overlapped sheets with a pencil, a reddish black image emerged on the developer coated surface. The developed color image had practically no problems with respect to resistance to light, moisture and $NO_x$.

EXAMPLE 21

[Preparation of pressure-sensitive recording paper using Type II crystals of crystalline toluene adduct of the compound of Formula (I-1)]

A CB sheet and a CF sheet were prepared carrying out the same procedures as described in Example 20 except that Type II crystals of the crystalline toluene adduct of the compound of formula (I-1) were used in place of the Type I crystals of the compound of Formula (I-1). A color image was developed by the same procedures as in Example 20. The developed color image had practically no problems with respect to resistance to light, moisture and $No_x$.

EXAMPLE 22

[Preparation of pressure-sensitive recording paper using Type III crystals of the compound of Formula (I-2)]

A CB sheet and a CF sheet were prepared carrying out the same procedures as described in Example 20 except that Type III crystals of the compound represented by the formula (I-2) were used in place of the Type I crystals of the compound of Formula (I -2). A color image was developed by the same procedures as in Example 20. The developed color image had practically no problems with respect to resistance to light, moisture and $No_x$.

EXAMPLE 23

[Preparation of pressure-sensitive recording paper using Type IV crystals of crystalline toluene adduct of the compound of Formula (I-2)]

A CB sheet and a CF sheet were prepared carrying out the same procedures as described in Example 20 except that Type IV crystals of the crystalline toluene adduct of the compound of Formula (I-2) were used in place of the Type I crystals of the compound of Formula (I-1). A color image was developed by the same procedures as in Example 20. The developed color image had practically no problem on the resistance to light, moisture and $NO_x$.

EXAMPLE 24

[Preparation of pressure-sensitive recording paper using Type V crystals of the compound of Formula (I-3)]

A CB sheet and a CF sheet were prepared carrying out the same procedures as described in Example 20 except that Type V crystals of the compound of Formula (I-3) were used in place of the Type I crystals of the compound of Formula (I-1). A color image was developed by the same procedures as in Example 20. The developed color image had practically no problem on the resistance to light, moisture and $NO_x$.

EXAMPLE 25

[Preparation of pressure-sensitive recording paper using Type VI crystals of crystalline toluene adduct of the compound of Formula (I-3)]

A CB sheet and a CF sheet were prepared carrying out the same procedures as described in Example 20 except that Type VI crystals of the crystalline toluene adduct of the compound Of Formula (I-3) were used in place of the Type I crystals of the compound of Formula (I-1). A color image was developed by the same procedures as in Example 20. The developed color image had practically no problems with respect to resistance to light, moisture and $NO_x$.

EXAMPLE 26

[Preparation of pressure-sensitive recording paper using Type VII crystals of crystalline toluene adduct of the compound of Formula (I-3)]

A CB sheet and a CF sheet were prepared carrying out the same procedures as described in Example 20 except that Type VII crystals of the crystalline toluene adduct of the compound of Formula (I-3) were used in place of the Type I crystals of the compound of Formula (I-1). A color image was developed by the same procedures as in Example 20. The developed color image had practically no problems with respect to resistance to light, moisture and $NO_x$.

What is claimed is:

1. A recording material comprising a support having at least one layer therein containing a chromogenic fluoran compound of the formula (I)

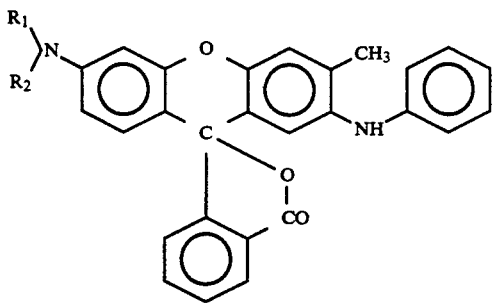

(I)

wherein $R_1$ and $R_2$ are different groups and are selected form cyclohexyl, n-butyl and isobutyl.

2. The recording material of claim 1, wherein in the fluoran compound of formula (I) $R_1$ is cyclohexyl and $R_2$ is n-butyl.

3. The recording material of claim 1, wherein in the fluoran compound of formula (I) $R_1$ is cyclohexyl and $R_2$ is isobutyl.

4. The recording material of claim 1, wherein in the fluoran compound of formula (I) $R_1$ is n-butyl and $R_2$ is isobutyl.

5. The recording material of claim 1, wherein the fluoran compound of formula (I) is in crystalline form.

6. The recording material of claim 5, wherein in the fluoran compound of formula (I) $R_1$ is cyclohexyl and $R_2$ is n-butyl, and the X-ray diffraction diagram by Cu-K $\alpha$ beams of the crystalline form of the fluoran compound indicates a high peak at a diffraction angle $2\theta$ of 9.2°, 15.2°, 18.5°, 19.5°, 19.9° and 21.8', and a relatively high peak at 19.1° and 22.8°.

7. The recording material of claim 5, wherein in the fluoran compound of formula (I) $R_1$ is cyclohexyl and $R_2$ is isobutyl, and the X-ray diffraction diagram by Cu-K$\alpha$ beams of the crystalline form of the fluoran compound indicates a high peak at a diffraction angle $2\theta$ of 7.9° and 19.0° and a relatively high peak at 17.0°, 20.3° and 24.1°.

8. The recording material of claim 5, wherein in the fluoran compound of formula (I) $R_1$ is n-butyl and $R_2$ is isobutyl, and the X-ray diffraction diagram by Cu-K $\alpha$ beams of the crystalline form of the fluoran compound indicates a high peak at a diffraction angle $2\theta$ of 6.7°, 11.6°, and 20.7°, and a relatively high peak at 12.1°, 18.2° and 21.3°.

9. The recording material of claim 1, wherein the fluoran compound of formula (I) is in the form of a crystalline toluene adduct.

10. The recording material of claim 9, wherein in the fluoran compound of formula (I) $R_1$ is cyclohexyl and $R_2$ is n-butyl and the X-ray diffraction diagram by Cu-K$\alpha$ beams of the crystalline form of the fluoran compound indicates a high peak at a diffraction angle $2\theta$ of 5.5°, 9.5°, 17.7°, 18.7°, 19.1° and 19.6°, and a relatively high peak at 11.8°, 15.3°, 21.0°, 23.4°, 23.7° and 24.2°.

11. The recording material of claim 9, wherein in the fluoran compound of formula (I) $R_1$ is cyclohexyl and $R_2$ is isobutyl and the X-ray diffraction diagram by Cu-K$\alpha$ beams of the crystalline form of the fluoran compound indicates a high peak at a diffraction angle $2\theta$ of 6.0°, and a relatively high peak at 11.2°, 13.3°, 16.4°, 18.5°, 19.0° and 20.6°.

12. The recording material of claim 9, wherein in the fluoran compound of formula (I) $R_1$ is n-butyl and $R_2$ is isobutyl, and the X-ray diffraction diagram by Cu-K$\alpha$ beams of the crystalline form of the fluoran compound indicates a high peak at a diffraction angle $2\alpha$ of 5.7° and a relatively high peak at 17.8°, 18.7°, 20.3° and 24.4°.

13. The recording material of claim 9, wherein in the fluoran compound of formula (I) $R_1$ is n-butyl and $R_2$ is isobutyl, and the X-ray diffraction diagram by Cu-K$\alpha$ beams of the crystalline form of the fluoran compound indicates a high peak at a diffraction angle $2\alpha$ of 6.3° and a relatively high peak at 13.2°, 16.4°, 20.3° and 20.6°.

* * * * *

UNITED STATES PATENT AND TRADEMARK OFFICE
CERTIFICATE OF CORRECTION

PATENT NO. : 5,324,704
DATED : June 28, 1994
INVENTOR(S) : Masakatsu NAKATSUKA et al.

It is certified that error appears in the above-indentified patent and that said Letters Patent is hereby corrected as shown below:

Claim 12; column 24, line 32: Delete "$\alpha$" after 2 and insert -- $\theta$ --.

Claim 13; column 24, line 39: Delete "$\alpha$" after 2 and insert -- $\theta$ --.

Claim 13; column 24, line 40: Delete " 20.3° ".

Signed and Sealed this

Twenty-sixth Day of September, 1995

*Attest:*

BRUCE LEHMAN

*Attesting Officer*       *Commissioner of Patents and Trademarks*